United States Patent
Kasten (10) Patent No.: US 10,913,967 B2
(45) Date of Patent: Feb. 9, 2021

(54) POINT-OF-CARE IN-VITRO DIAGNOSTIC DEVICE FOR THE AMPEROMETRIC DETECTION OF CHOLINESTERASE ACTIVITY IN WHOLE BLOOD FOR INDICATION OF EXPOSURE TO CHOLINESTERASE INHIBITING SUBSTANCES

(71) Applicant: The Government of the United States, as represented by the Secretary of the Army, Fort Detrick, MD (US)

(72) Inventor: Shane Aaron Kasten, Fallston, MD (US)

(73) Assignee: The Government of the United States, as represented by the Secretary of the Army, Ft. Detrick, MD (US)

( * ) Notice: Subject to any disclaimer, the term of this patent is extended or adjusted under 35 U.S.C. 154(b) by 0 days.

(21) Appl. No.: 16/202,755

(22) Filed: Nov. 28, 2018

(65) Prior Publication Data

US 2019/0292576 A1  Sep. 26, 2019

Related U.S. Application Data

(60) Provisional application No. 62/591,457, filed on Nov. 28, 2017.

(51) Int. Cl.
*G01N 27/327* (2006.01)
*C12Q 1/00* (2006.01)
*C12N 9/18* (2006.01)

(52) U.S. Cl.
CPC ............ *C12Q 1/005* (2013.01); *C12N 9/18* (2013.01); *C12Q 1/002* (2013.01); *G01N 27/3272* (2013.01); *C12Y 301/01007* (2013.01)

(58) Field of Classification Search
CPC ... G01N 27/327–3272; G01N 21/8483; C12Q 1/005
See application file for complete search history.

(56) References Cited

U.S. PATENT DOCUMENTS

| 6,746,850 B2 | 6/2004 | Feaster et al. | |
| 2011/0284374 A1* | 11/2011 | Krejci | G01N 33/4875 204/408 |
| 2017/0258378 A1* | 9/2017 | Eshoo | A61B 5/14735 |

OTHER PUBLICATIONS

Mesulam et al., "Anatomy of Cholinesterase Inhibition in Alzheimer's Disease: Effect of Physostigmine and Tetrahydroaminoacridine on Plaques and Tangles," Annals of Neurology vol. 22, No. 6, Dec. 1987 (Year: 1987).*

(Continued)

*Primary Examiner* — Alexander S Noguerola
(74) *Attorney, Agent, or Firm* — Leigh Z. Geltender (57) ABSTRACT

A system that can assess red blood cell AChE activity to provide warning of exposure and possibly inform treatment with medical countermeasures is disclosed. A portable, ideally hand-held, in vitro diagnostic point of care system capable of electrochemically-based detection of red blood cell acetylcholinesterase (AChE) activity from an undiluted whole blood sample provides a real-time pre-symptomatic warning of exposure to organophosphorus nerve agent or other poison, such as a pesticide, which informs treatment with medical countermeasures. One preferred version of the invention provides a system that uses highly stable test strips and a lightweight, low power hand-held potentiostat detector. The disclosed invention provides a real-time quantitative assessment of cholinesterase (ChE) enzymatic activity directly from a small whole blood sample for indication of exposure to ChE inhibiting substances (i.e., chemical warfare nerve agents or carbamate pesticides), thereby allowing (Continued)

immediate assessment of a blood sample in the field during the pre-symptomatic window.

20 Claims, 9 Drawing Sheets

(56) References Cited

OTHER PUBLICATIONS

EQM Research Inc., "Test-mate ChE Cholinesterase Test System (Model 400) Instruction Manual," www.eqmresearch.com, pp. 1-31, 2003.
EQM Research Inc., "AChE Erythrocyte Cholinesterase Assay Kit (Model 460)," & "PChE Plasma Cholinesterase Assay Kit (Model 470) Package Insert," www.eqmresearch.com, WebInsert-D, pp. 1-4, 2003.
EQM Research Inc., "Description of the Test-mate ChE," www.eqmresearch.com, pp. 1-3, 2003.
Jeyaratnam J., "Acute pesticide poisoning: A major global health problem", World Health Stat Quart 43(3):139-144 (1990).
Massoulie et al., "The Molecular Forms of Cholinesterase and Acetylcholinesterase in Vertebrates", Ann. Rev. Neurosci., 1982, 5:57-106.

\* cited by examiner

POINT-OF-CARE IN-VITRO DIAGNOSTIC DEVICE FOR THE AMPEROMETRIC DETECTION OF CHOLINESTERASE ACTIVITY IN WHOLE BLOOD FOR INDICATION OF EXPOSURE TO CHOLINESTERASE INHIBITING SUBSTANCES

RELATED APPLICATIONS

This application claims the benefit of priority of U.S. Provisional Patent Application No. 62/591,457, filed on Nov. 28, 2017. The entire content of which is incorporated by reference as part of the disclosure of this application.

STATEMENT OF GOVERNMENT INTEREST

The invention described herein may be manufactured, used and licensed by or for the United States Government.

BACKGROUND OF THE INVENTION

Acute exposure to cholinesterase (ChE) inhibitors results in rapid inhibition of cholinesterase activity in systemic circulation followed by inhibition of AChE at the neuronal synapse, eventually resulting in cholinergic crisis. Detection and treatment is crucial following exposure since timely therapeutic intervention can avert irreversible neurological damage and death. Depending on the type of inhibitor and route of exposure, the enzymatic activity of red blood cells associated AChE can be completely inhibited well before overt signs or symptoms are evident. The inhibition status of red blood cell AChE activity provides a convenient biosensor and diagnostic biomarker of exposure. Current medical doctrine advises immediate medical treatment to individuals with blood cholinesterase activity levels below 50% of unexposed baseline level. Pretreatment with pyridostimine will decrease red blood cell AChE activity altering the average or personal baseline so rapid assessment prior to entering the field will help inform treatment in an exposure event. Thus, immediately following exposure (inhalation and/or dermal), cholinesterase inhibitors diffuse into systemic circulation and rapidly inhibit blood cholinesterase enzymes (acetylcholinesterase (AChE), butyrylcholinesterase (BChE)). There can be several minutes to hours before overt signs or symptoms, due to the peripheral and central cholinergic response, can be detected. The duration of this pre-symptomatic window is dependent on the extent and type of the exposure.

As explained in U.S. Pat. No. 6,746,850—Feaster, et al., cholinesterases (ChEs) are highly polymorphic carboxylesterases of broad substrate specificity, involved in the termination of neurotransmission in cholinergic synapses and neuromuscular junctions. Some ChEs terminate the electrophysiological response to the neurotransmitter acetylcholine by rapidly degrading it, while the precise function of others is unknown. ChEs are classified into acetylcholinesterase (AChE) and butyrylcholinesterase (BChE) according to their substrate specificity and sensitivity to selective inhibitors. See Massoulie, J., et al., (1982) Ann. Rev. Neurosci. 5:57-106, which is incorporated herein by reference. Nerve agents, chemical warfare agents, organophosphates (OPs), pesticides, insecticides, and other such noxious chemicals exert their toxic effects by inhibiting AChE, BChE, or both. Plasma BChE and erythrocyte AChE provide some protection to synaptic AChE from these neurotoxins by scavenging free circulating AChE toxins, BChE toxins, or both prior to absorption into the central and peripheral nervous systems. Only the non-scavenged neurotoxins are capable of attacking synaptic AChE. Therefore, a subject's susceptibility to these neurotoxins may be determined by measuring the concentrations and activities of AChE and BChE in the subject. Additionally, exposure to these neurotoxins may be determined by measuring the concentration and activity of AChE, BChE, or both in a subject suspected of being exposed.

Currently no far-forward in vitro diagnostic (IVD) test systems are practical for use in the field to determine, during the pre-symptomatic window, exposure to substances that inhibit cholinesterase (ChE). Accordingly, there is a need to provide an ultraportable, low complexity point-of-care (POC) in-vitro diagnostic (IVD) device for the real-time quantitative assessment of cholinesterase (ChE) enzymatic activity via whole blood from a finger stick as an indication of exposure to ChE inhibiting substances (i.e., chemical warfare nerve agents or carbamate pesticides).

Systems are known for testing ChE, for example, the Test-mate ChE Cholinesterase Test System manufactured and sold by EQM Research, Inc. is directed to monitoring occupational exposure to pesticides. The Test-Mate system is only intended for monitoring exposure to pesticides. The system requires 10 µL for each blood test, from a fingerstick sample, and the blood is then diluted and mixed with reagents in vials before testing, the overall process requires about 10 steps and takes over four minutes per sample. The device is portable but relatively cumbersome having dimensions of (11"×7"×10") and weighing (10 pounds), in other words it is not small enough to tuck into a medical bag.

The Test-Mate system uses a methodology known as Ellman's Assay and a colorimetric detection system. This system is also burdensome to the operator as it requires dry reagent to be dissolved in water using a water dropper and plastic pipette thus requiring sample preparation prior to conducting a measurement. Thus, the Test-Mate system provides a diagnostic system for determining ChE inhibition in extracted blood following exposure that utilizes acetylthiocholine (ATCh) and Ellman's reagent (DTNB) to spectrophotometrically determine red blood cell AChE activity utilizing the chemical redox potential of thiocholine. Although an accurate diagnostic system in the laboratory, the current version of the Test-Mate system utilizes antiquated hardware, involves numerous steps to process a single sample, and requires a substantial amount of space when being used. The Test-Mate system correlates the thiocholine oxidation of DTNB and resulting change in absorbance (450 nm) to the activity/inhibition status of red blood cell AChE from a 10 µL sample of whole blood (that has been substantially diluted by reagents) over a four (4) minute process time.

Therefore, an objective of the present invention is to provides a portable, ideally hand-held in vitro diagnostic (IVD) point of care (POC) system capable of electrochemically-based detection of red blood cell (RBC) acetylcholinesterase (AChE) activity from a whole blood sample to provide a real-time pre-symptomatic warning of exposure to organophosphorus nerve agent or other poison, such as a pesticide, which could be used to inform treatment with medical countermeasures.

SUMMARY OF THE INVENTION

In response to the need stated above, the present invention provides a point-of-care (POC) in-vitro diagnostic (FM) device for the real-time quantitative assessment of cholinesterase (ChE) enzymatic activity in whole blood for indication of exposure to ChE inhibiting substances (i.e., chemical warfare nerve agents or carbamate pesticides). This device allows assessment of a blood sample during the pre-symptomatic window providing early warning of a suspected exposure and a possible trigger-to-treat with a medical countermeasure.

The present invention may also be utilized to differentiate between types of exposure when symptomatologies can have similar manifestation, such as pinpoint pupils, which can be evident following exposure to other chemical agents besides ChE inhibiting substance such as a synthetic opioid overdose).

The present invention can, preferably, operate and share most of the physical attributes of current self-monitoring blood glucose (SMBG) test systems (i.e., glucometer and glucose test strips). As with blood glucose test systems, the present invention utilizes microliter amounts of capillary blood from a finger stick, ChE-test strips (similar to glucose test strips), and a hand-held potentiostat (similar to a glucometer) in order to take a measurement. Blood from a lanced finger is applied to the end of the ChE-test strip, allowing the ChE enzymes to mix with reagent(s) over the surface of printed electrodes. The ChE-test strip consists of two (working and pseudo-reference) or three (working, reference, counter) electrodes. An electron mediator may also be incorporated into the working and counter electrodes to facilitate electron transfer to and from an electroactive ChE reaction component.

The reagents involved in the measurement are dry coated on the electrode surface, thus no sample preparation (such as blood sample dilution) or liquid-liquid mixing of any kind is needed prior to assessment in contrast to the above-described EQM Test-mate system. In particular, one of two possible reagent substrates, acetylthiocholine (ATCh) or butyrylthiocholine BTCh), are dry coated on to the ChE-test strips depending on the ChE activity (AChE and/or BChE) being assessed. Another reagent component that may be dry coated on the electrodes is bambuterol, which is a selective inhibitor of the BChE enzyme, bambuterol is very effective, highly soluble, has long shelf life. Various BChE specific inhibitors have been tested to include, ethopropazine, rivastigmine, iso-OMPA, (–)-$N^1$—$N^8$-bisnorcymserine, and (–)-$N^1$-phenethylcymserine. The incorporation of a BChE-specific inhibitor will be utilized when only assessments of AChE activity are desired. It should be noted that some people are deficient in BChE, but it is still useful to test for it. The ChE-test strip may also include a second set of electrodes to allow simultaneous assessment of blood hematocrit levels for normalization of AChE activity measurements. Surfactants are also utilized in the reagent formulation as wetting-agents. The surfactants tested have hydrophilic lipophilic balance ("HLB") values between 4 and 20 including but not limited to Tween-20, Tween-80, Tergitol N10, Brij 93, Merpol A/SE, and Pluronic L-35/F-108/F68.

The ChE-test strips used in the present invention form an electrochemical sensor allowing the chemical conversion of ATCh or BTCh to be transduced into an electrical signal since one of the chemical products of the reaction, known as thiocholine, is electroactive. In the present invention, the thiocholine oxidizes the electron mediator, cobalt phthalocyanine, which in turn undergoes oxidization directly at the carbon electrode surface; causing a change in amperage due to the influx of electrons; however, the present invention is also useful without an electron mediator. The amperage change is measured using a chronoamperometric technique via a hand-held potentiostat operating with a custom software algorithm and custom hardware.

The present invention provides a system that uses highly stable test strips and a lightweight, low power hand-held potentiostat detector (similar to glucometer and glucose test strips). The assessment of AChE preferably takes less than 30 seconds, which is eight times faster than the systems found in the prior art. An important advantage of the present invention is that the data are collected from an undiluted sample of less than 5 μl of whole blood (i.e., capillary blood). Because of the ease of use and speed to results, the present invention provides pre-symptomatic early warning of cholinesterase inhibitor exposure, that is, trigger-to-treat with medical countermeasures. By using electrochemically-based detection the system disclosed herein avoids fragile optics and blanking controls. The simplicity of the present invention results in the ability to perform low effort self-monitoring with no specialized training required. In use, the invention permits rapid personal red blood cell AChE baseline after pretreatment (e.g. pyridostigmine).

BRIEF DESCRIPTION OF THE DRAWINGS

Like reference symbols and designations in the various drawings indicate like elements.

DETAILED DESCRIPTION

As explained above and set forth in further detail below, currently no practical in vitro diagnostic (IVD) test systems are available to give indication of exposure to substances that inhibit cholinesterase (ChE) on the austere battlefield. Blood cholinesterase levels can become significantly depressed prior to the onset of signs/symptoms of intoxication, presenting a physiological biosensor of exposure, which, if assessed, could potentially provide a trigger-to-treat with a medical countermeasure ("MCM"), thus preventing irreversible neurological damage or death. Electrochemical-based detection of cholinesterase activity in whole blood is a potential methodology that provides a rapid, low burden, and simple assessment amenable to "Role 1" treatment. As used herein, Role 1 means point of injury care, or what might normally be described as "first responder care," that is, first-aid and immediate lifesaving measures provided by self-aid, buddy aid, or a combat lifesaver (non-medical team/squad member trained in enhanced first-aid).

A fundamental evaluation and feasibility study determined if amperometric detection could be harnessed to assess ChE activity in blood, preferably in undiluted whole blood, utilizing commercial screen-printed electrodes (SPEs) in combination with a benchtop potentiostat. Various types of SPEs (unmodified, modified, electron-mediated) were screened to down-select to an electrode composition with analytical sensitivity and to define the optimal amperometric conditions for detecting the electroactive compound, thiocholine, in phosphate-buffered saline or in pooled whole blood collected from various animal models. A single electrode composition was selected based on both cyclic voltammetric and chronoamperometric measurements. An in-vitro diagnostic test system that does not require sample preparation in the field would lower the burden and complexity of an assessment. Reagent was dry-coated on the electrode surface of an SPE to determine if ChE activity measurements could be initiated by simply applying whole blood to the electrode without sample manipulation. Kinetic studies were conducted with human recombinant acetylcholinesterase and butyrylcholinesterase in conjunction with whole blood ChE to define assay conditions prompting optimal sensitivity for ChE activity measurements. Inhibition assessments of blood ChE were also carried out via ex vivo and in vivo studies following incubation or exposure to various chemical warfare nerve agents. The results supported development of a point-of-care IVD test system based on amperometric detection that could be employed for either buddy-monitoring or self-monitoring. Thus, modified, unmodified and electron mediated screen printed electrodes are useful with the present invention.

Figure 1:
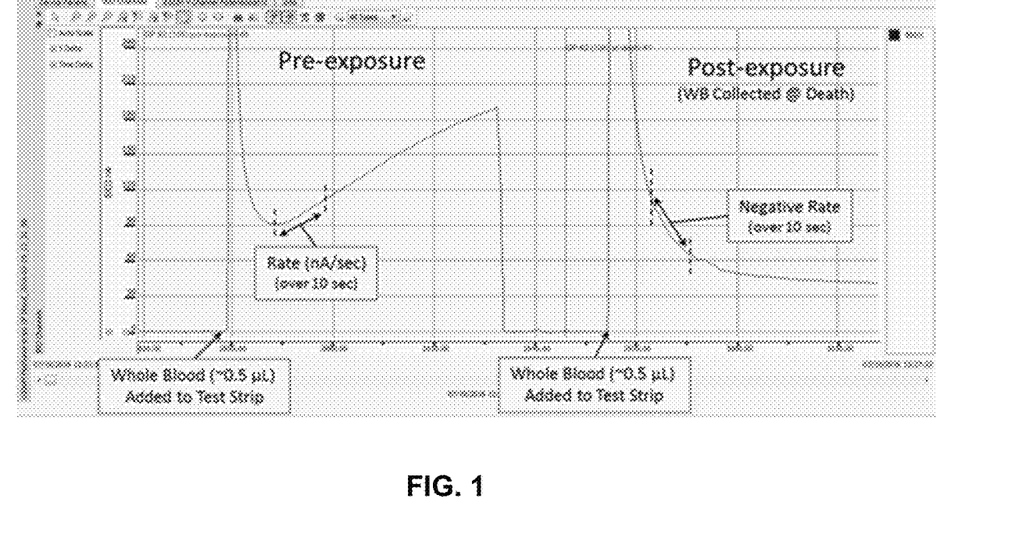
FIG. 1 shows cholinesterase (ChE) data as collected.
Figure 2:
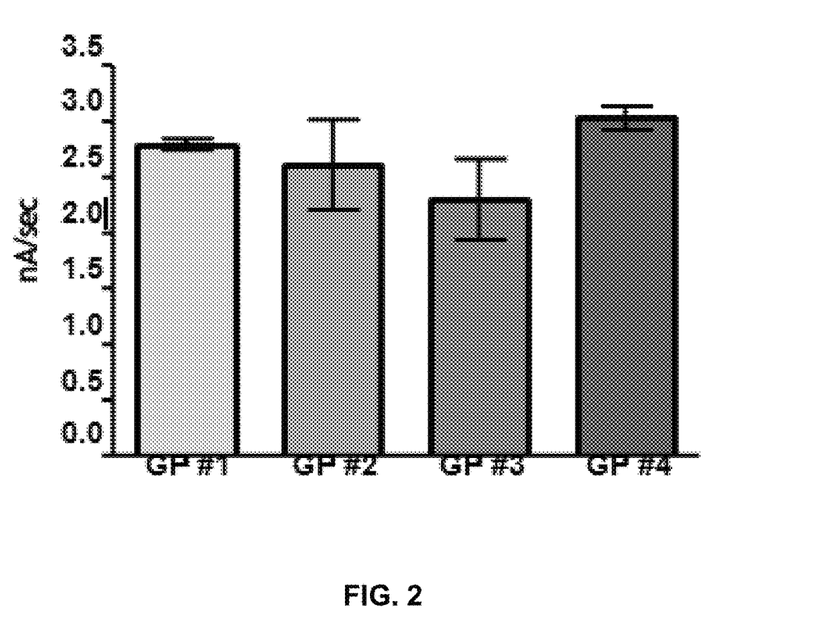
FIG. 2 shows baseline ChE activity levels for 4 guinea pigs.

Referring now to FIGS. 1-2, the results of the proof-of-concept of studies described above using repurposed commercially available glucose test strips to determine if cholinesterase (ChE) activity could be measured in whole blood from guinea pigs are illustrated. A benchtop potentiostat was utilized for amperometric measurements. An example of the raw data acquired is shown in FIG. 1. Baseline ChE activities measured for four (4) guinea pigs with the test bed are shown in FIG. 2.

Figure 3:
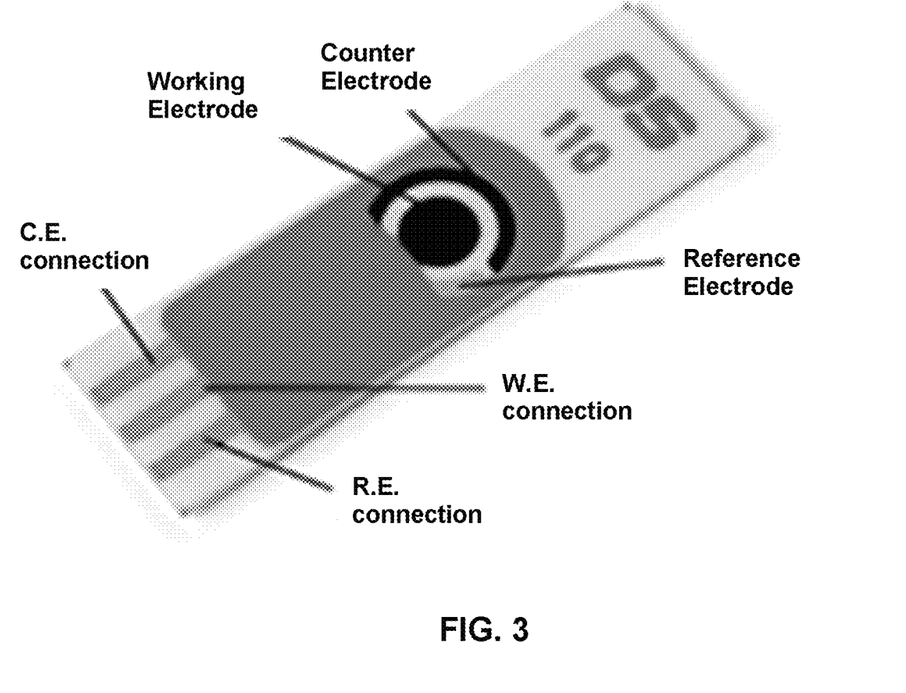
FIG. 3 shows a screen printed electrode.
Figure 4:
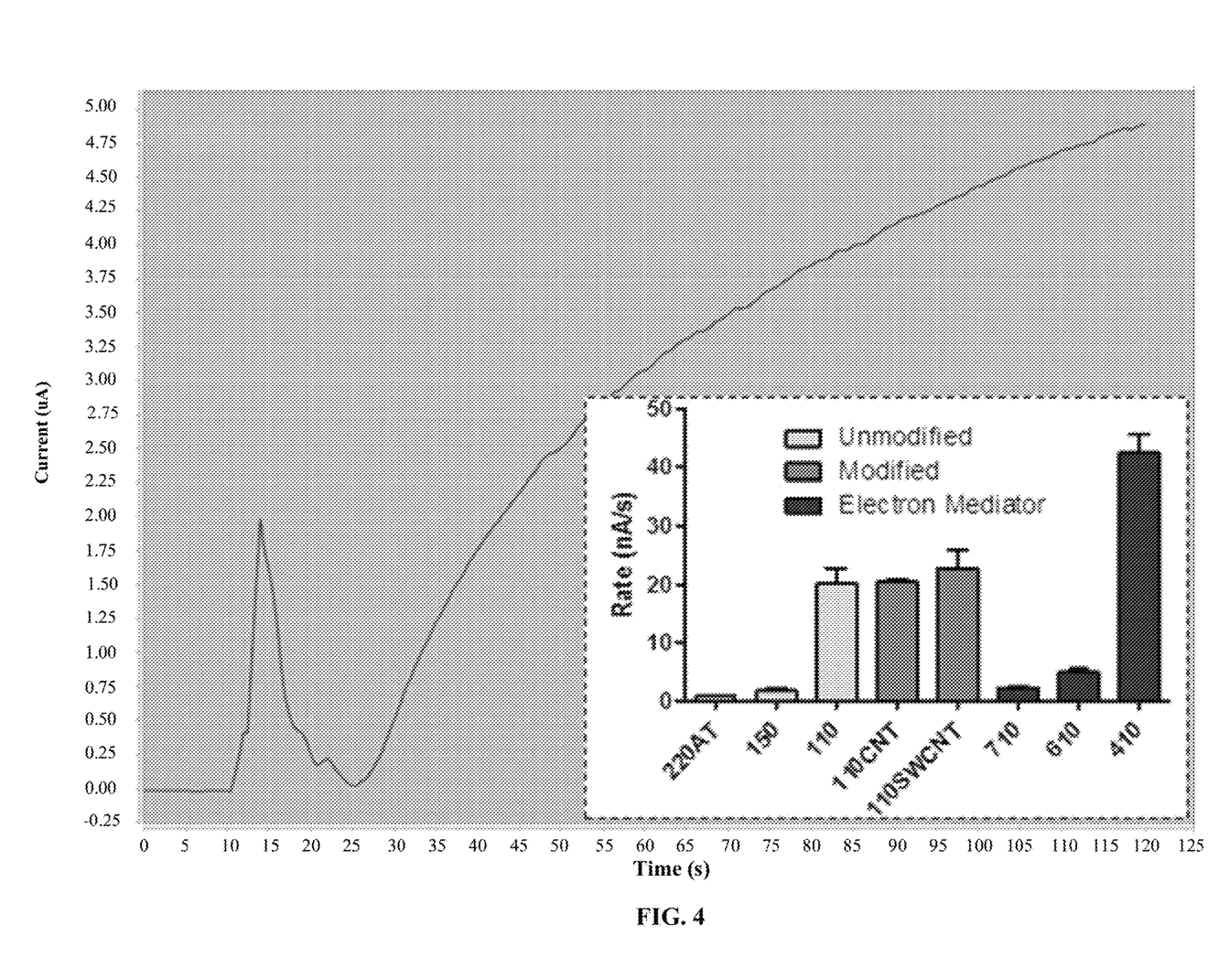
FIG. 4 shows chronoamperometric response for a screen printed electrode.

Several electrode chemistries are useful in conjunction with the present invention and the results of one such suitable chemistry for an AChE test strip are illustrated in FIGS. 3-4. Several commercially available screen-printed-electrodes were evaluated to find the electrode chemistry with the highest sensitivity ratio (i.e., those that provide the highest rate (current/sec) requiring the lowest voltage potential) as a result of cholinesterase-mediated thiocholine production and thus thiocholine oxidation at the electrode surface. Screen printed electrodes were purchased from DropSens (Oviedo, Spain) via Metrohm (Riverview, Fla.), however, the results described are not manufacturer dependent. It will be understood that using the lowest voltage potential eliminates or at least minimizes the problems resulting from electroactive interfering compounds. Thus, for one example, a raw carbon electrode, although useful, requires a high voltage potential and is more readily subjected to diminished results created by electroactive interfering compounds.

As seen in FIG. 3, screen printed electrodes typically have three electrodes: working, counter, and reference. All screen printed electrodes used silver (Ag) for the reference electrodes while three different working electrode chemistry types were tested; unmodified, modified, and with an electron mediator. The unmodified screen printed electrodes tested were: 110 (carbon), 220AT (gold), and 150 (platinum). Modified electrodes were the 110CNT (multi-walled carbon nanotubes) and the 110SWCNT (single-walled carbon nanotubes). Three carbon screen printed electrodes with electron mediators integrated into the working electrode were also tested: 410 (Co-phthalocyanine), 610 (Meldola's blue), and 710 (Prussian Blue). Of these three, 410 (Co-phthalocyanine) produced the best results with the systems and test procedures described in detail herein. All screen printed electrodes were prepared by depositing 5 μL of 100 mM acetylthiocholine (in 100% methanol) onto the working electrode followed by complete drying in a fume hood for 20 minutes. A voltage potential of 0.6 V was applied to each screen printed electrode prior to depositing 50 μL of guinea pig whole blood over the entire surface covering each electrode. A representative plot of the chronoamperometric response for a "410" (Co-phthalocyanine) screen printed electrode is shown in FIG. 4. To create the data shown in FIG. 4, blood was deposited 10 seconds after initiating data collection. A positive slope emerges at 25 seconds (15 seconds after blood is deposited) allowing a rate determination over the next 5 seconds for a total time of 20 seconds for measurement. Initial rates measured for each type of screen printed electrode are shown in the inset of FIG. 4. The highest rates were measured with the 110, 110CNT, 110SWCNT, and the "410" screen printed electrodes. In view of this result the first prototype AChE test strip used carbon ink integrated with the Co-phthalocyanine mediator, as found in the "410" screen printed electrode. From these results, a three electrode test strip design was created, using strips at a size of 10 mm×33 mm. The 10 mm width allows the strips to be tested via a desktop potentiostat so that a handheld device is not needed during the strip development phase.

Figure 5:
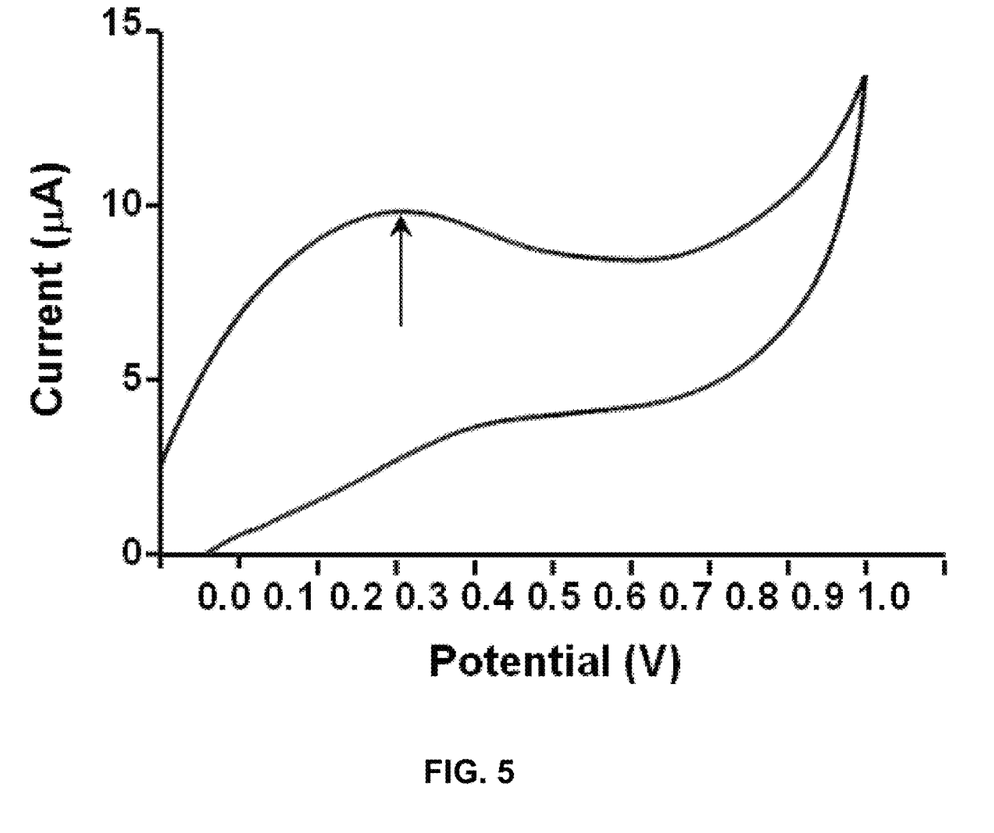
FIG. 5 shows voltage potential for thiocholine in whole blood.

Referring now to FIG. 5, the determination of an optimal voltage potential for thiocholine in whole blood is set forth. The optimal voltage potential for the oxidation of thiocholine in whole blood is determined using cyclic voltammetry. The goal is to determine the lowest voltage potential that gives the highest amperage response due to thiocholine oxidation. Thiocholine was prepared by incubating 20 mM acetylthiocholine (500 μL) with human recombinant acetylcholinesterase (15 μL, 1 mg/mL) at room temperature for 40 minutes. Thiocholine production was monitored via Ellman's reagent at 412 nm until accumulation of product ceased. The 20 mM thiocholine was mixed with guinea pig whole blood to obtain a final concentration of 2 mM. A negative control was generated by adding phosphate-buffered saline (100 mM PBS, pH 7.4) to whole blood at a volume equivalent to the 20 mM thiocholine. Both samples (20 μL) were deposited on screen printed electrodes followed by cycling the current from 0.0 V to 0.9 V and then cycled back down to 0.0 V. The scan rate was 0.5 V/s with amperage recorded in 0.002 V steps. The Faradaic current (upper line, cathodic current, moving from 0 V to 0.9 V) for thiocholine gave a peak with a maximum at 0.3 V as seen in FIG. 5. This peak is a result of thiocholine oxidation at the electrode surface. The negative control curve is not shown in FIG. 5. From these data, it was determined that an optimal voltage potential for thiocholine in guinea pig whole blood is 0.3 V. This voltage potential appears to be optimal and can be utilized for prototyping studies and development of diagnostic systems made in accordance with the present invention.

Figure 6:
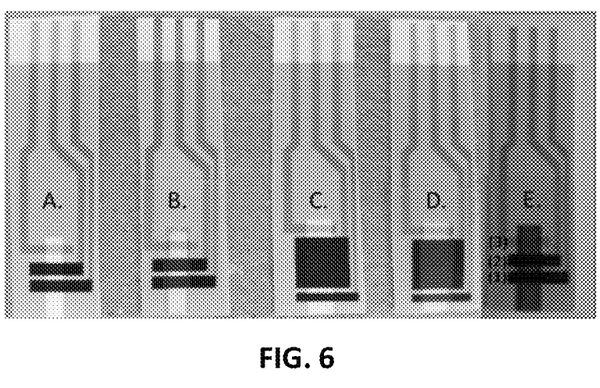
FIG. 6 shows a group of electrodes.

A screen printed electrode with Co-phthalocyanine as the electron mediator was identified as the most sensitive electrode chemistry for thiocholine in guinea pig whole blood. Prototyping of AChE-test strips was based on the selected screen printed electrode. Two prototype iterations were designed and produced. The design of the first prototype (P1) strip was loosely patterned around a three electrode arrangement with both the working and auxiliary electrodes printed with carbon ink containing Co-phthalocyanine. A second prototype design (P2) was also produced. Both P1 and P2 are shown in FIG. 6. The prototype strips were created in an unassembled format thus allowing deposition of choice reagents onto the electrode surface prior to full assembly with spacer and lid materials. Blood applied to the assembled strips crosses a counter electrode first, then moves the working electrode, and finally across the reference electrode (Ag/AgCl) before filling the strip chamber completely in less than one second, as seen in the right most portion of FIG. 6.

Figure 7:
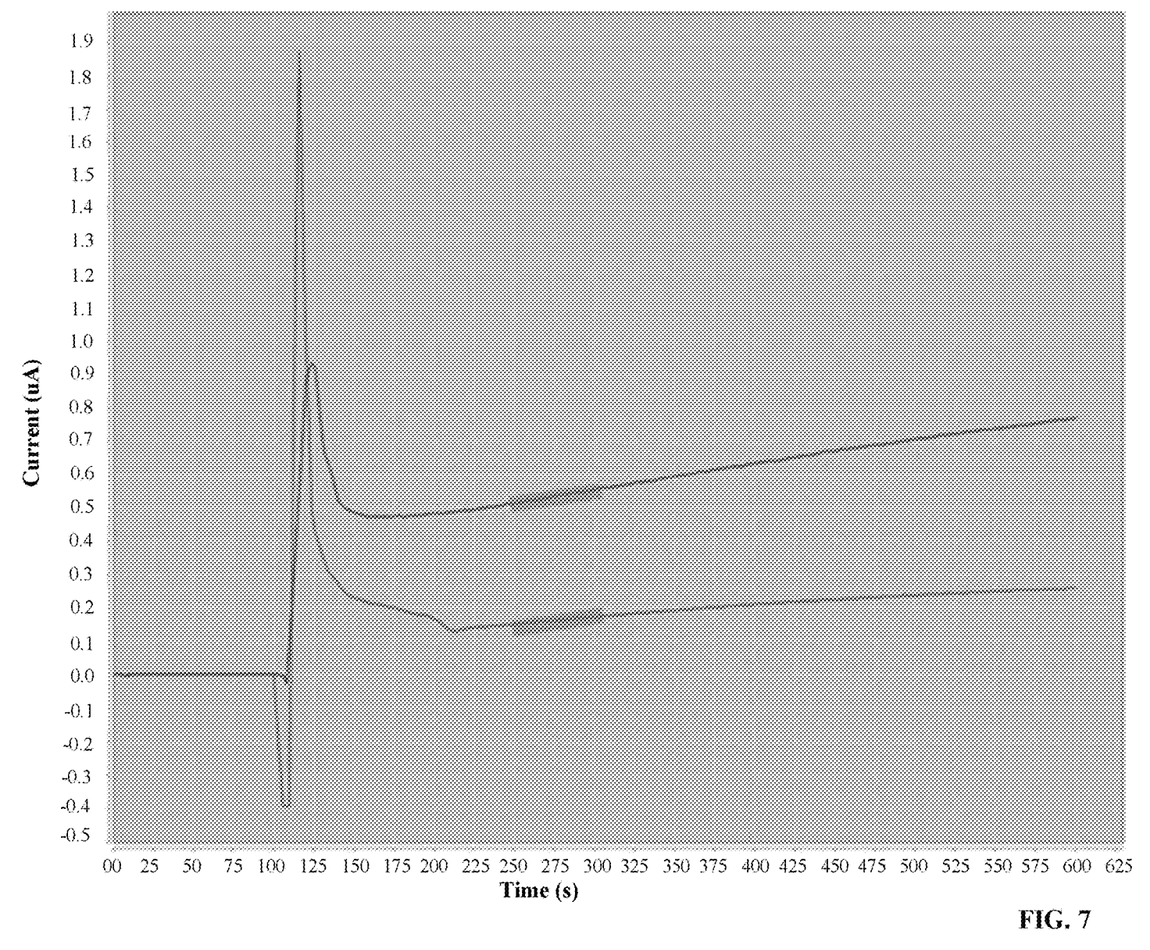
FIG. 7 shows current versus time for the electrodes of FIG. 6.

The strips were evaluated by assessing the activity of red blood cells (RBC AChE) in guinea pig whole blood. P1 strips were left unassembled and 2 µl of 10 mM acetylthiocholine (ATCh) was dry coated on the working electrode. The initial velocity for RBC AChE was assessed with a screen printed electrode by preparing the working electrode in the same manner and which served as a direct comparison with the unassembled P1 strip. A volume of 40 4 of whole blood was spread over the electrodes with a voltage potential of 0.35 V. Amperometric profiles for both P1 (lower curve) and the screen printed electrode (upper curve) are shown in FIG. 7. The portions of the linear slope measured as the initial velocity for RBC AChE are covered with grey boxes. The initial velocity measured for the screen printed electrode screen printed electrode (8.4 nA/sec) was 2.5 times higher than for the unassembled P1 strip (3.4 nA/sec). It was assumed that the difference in measured velocity was due to the larger surface area of the working electrode of the screen printed electrode screen printed electrode. The working electrode (a 4 mm diameter circle) of the screen printed electrode has a surface area of 12.5 $mm^2$, respectively. The total surface area of the P1 working electrode is 9 $mm^2$ when left unassembled and 3 $mm^2$ when assembled. During the assessment only about 6 $mm^2$ of the P1 working electrode was covered by whole blood. The ratio of the working electrode surface areas (screen printed electrode/P1=12.5/6) contributing to the measurement in the comparison was calculated to be about 2.1. A near linear relationship between the working electrode surface area and the measured rate was assumed based on the relationship found for the approximately 2.1 times larger surface area in proximate agreement with the approximately 2.5 times higher rate measured with the screen printed electrode screen printed electrode. Based on these results a second prototype strip, P2, was designed with a working electrode surface area 6 times greater than the P1 working electrode to try to amplify the baseline RBC AChE activity signal magnitude for guinea pig blood. When left unassembled the working electrode of the P2 strip was designed to have a surface area of 30 $mm^2$ and when fully assembled an available surface area of 18 $mm^2$.

A direct comparison of the P1 and P2 strips was conducted using guinea pig whole blood. The initial rates measured for the unassembled P2 strips were estimated to be about 6× higher than for the unassembled P1 strips based on the apparent linear relationship between working electrode surface area and magnitude of initial rate as indicated above. The hypothesis did hold as seen in Table 1 in which the unassembled P2 initial rate was 6 times higher than that of the unassembled P1 strip.

TABLE 1

| Prototype | RBC AChE Initial Rate (nA/sec) | |
|---|---|---|
| | Unassembled | Assembled |
| P1 | 4.5 | 21.4 |
| P1 | 27.0 | 26.2 |

An unexpected enhancement of nearly five times (approximately 4.8×) in initial rate magnitude was also found when comparing the assembled P1 strip versus the unassembled P1 strip. Unfortunately, this same enhancement was not evident for the P2 strip after assembly. These results indicated that the difference in initial rate magnitude was marginal between the assembled P1 and P2 strips; even with the 6× larger WE surface area in the P2 strip.

Figure 8:
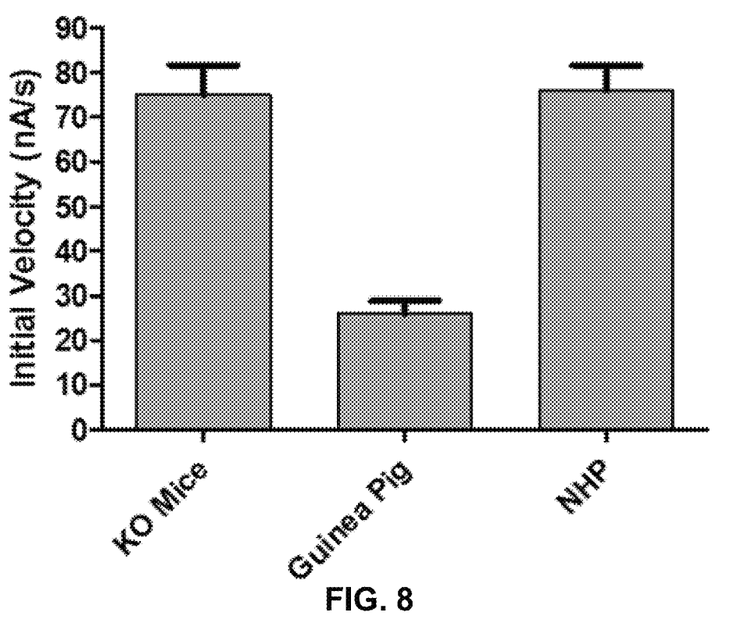
FIG. 8 shows the performance of test strips in various animals.

A limited comparison of red blood cell AChE initial velocities was conducted with mouse (C57BL6), guinea pig, and non-human primate (NHP) whole blood using assembled P1 test strips, the results of which are shown graphically in FIG. 8. The pooled mouse blood tested in this study used mice from a colony that are a carboxyesterase knock-out (KO) on the C57BL6 background strain. Whole blood from the wild-type C57BL6 was not available at the time of assessment and it was assumed that the lack of carboxyesterase does not influence the red blood cell AChE activity however this assumption will be tested when blood becomes available. It was also assumed that NHP whole blood would be a suitable substitute for human blood thus any measured red blood cell AChE activity would be very similar. The NHP blood tested in this study was obtained from a pool of three NHPs. All assessments were conducted in triplicate. Both the KO mice and the NHP shared nearly the same initial velocity magnitude while the guinea pig gave a three times slower rate. This result supports the use of the mouse (C57BL6) or KO mouse as an animal model, instead of the guinea pig, for further pre-clinical evaluation of a test system (test strips and hand-held potentiostat) since the red blood cell AChE activity measured in the KO mouse was so similar to the NHP.

Figure 9:
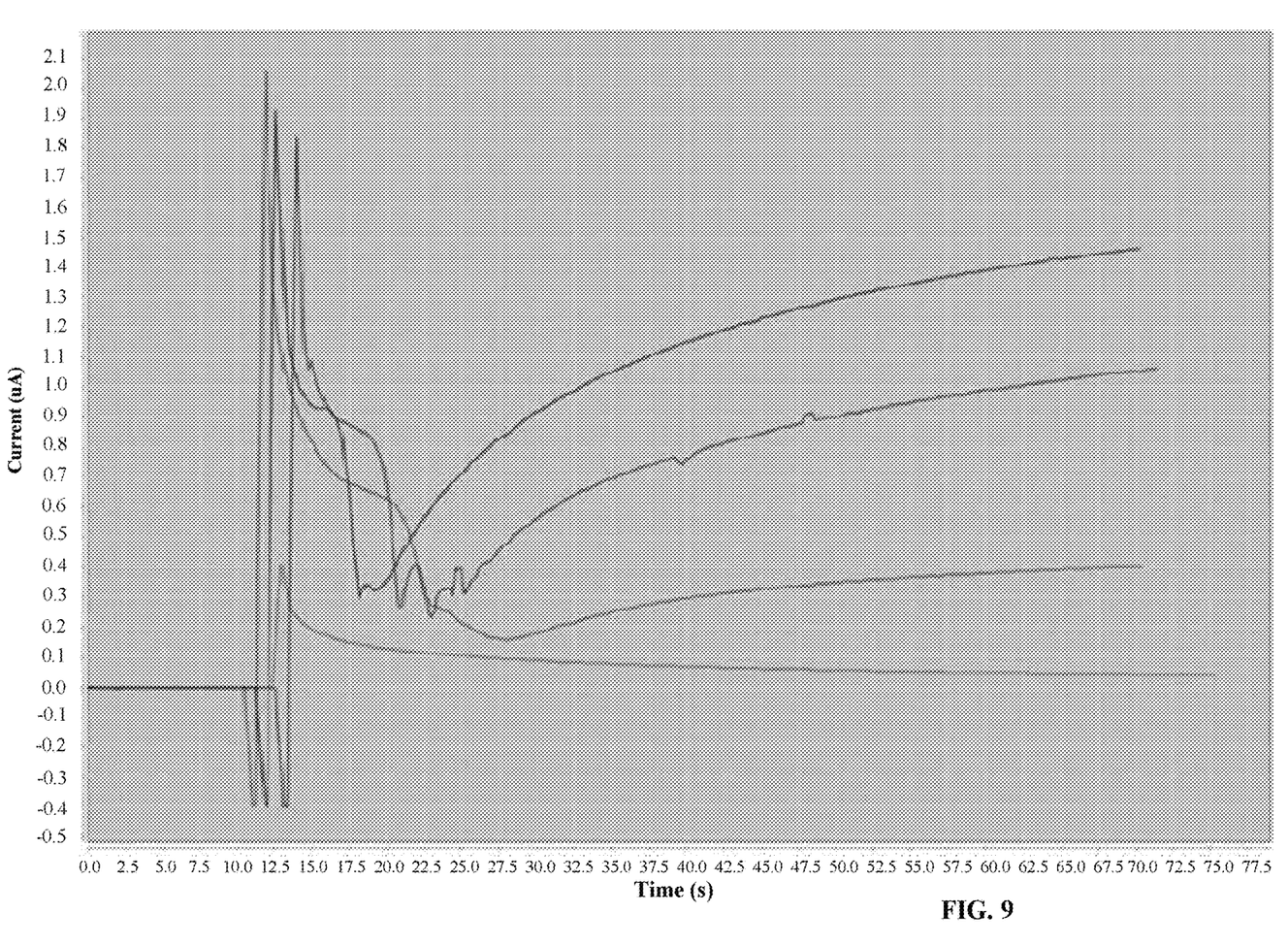
FIG. 9 shows current versus time for the data of FIG. 8.

Studies next determined the conditions for conducting ex vivo measurements of red blood cell AChE activity after inhibition of whole blood with an organophosphorus nerve agent. A small stock of inhibited whole blood was obtained by incubating 1.0 mL of KO mouse blood with 1.0 µL of GB (sarin) (pure P(−) isomer) for 10 minutes at room temperature. The amperometric profiles for four different conditions using the P1 test strip described above are shown in FIG. 9. The top profile shows the response for uninhibited whole blood with an initial velocity of ~70.4 nA/sec. The bottom curve represents what a fully inhibited blood profile would look like—no ATCh was dry coated on the working electrode in this case. The next to bottom curve shows the profile for the inhibited blood after the 10 minute incubation with an initial velocity of 14.4 nA/sec, which constitutes an approximately 80% inhibition. There was no change in the initial velocity of this sample when re-assessed 50 minutes later. A 50/50 mixture of uninhibited and inhibited blood was then made by adding equal volumes together, and the results are the curve one down from the top. The rate was immediately measured giving an initial rate of about 48.3 nA/sec which constitutes an approximately 32% inhibition. This level of inhibition was slightly below the 40% inhibition expected for the mixture ratio. Overall the P1 test strips in combination with the mouse blood will provide a viable system for further ex vivo inhibition studies, algorithm development and optimization, and for direct method comparison with existing alternatives or competitive systems.

As seen from the foregoing, two different AChE-test strip prototypes (P1 and P2) were used to determine useful parameters for the present invention. While a linear relationship between the working electrode surface area and red blood cell AChE initial velocity was supported by unassembled test strips this relationship does not appear to have been maintained when the strips were fully assembled. A limited comparison of red blood cell AChE baseline in whole blood of mice, guinea pig, and NHP demonstrated that mouse blood was a better match with NHP blood prompting a switch of animal model for pre-clinical testing from guinea pigs to mice. An ex vivo study was conducted to begin developing experimental conditions for testing whole blood at various levels of inhibition using the P1 test strips and mouse blood to help support algorithm development and method comparison with alternative systems.

Figure 10:
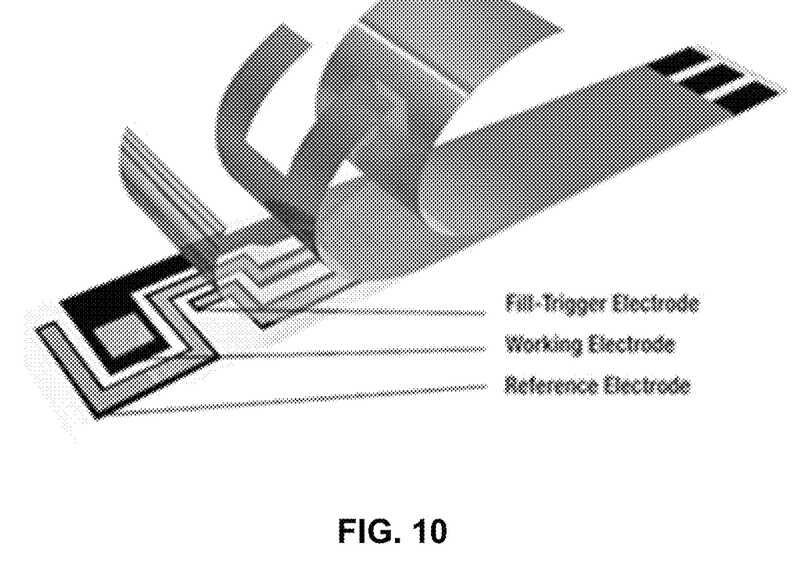
FIG. 10 shows an exploded perspective view of the electrodes in a test strip made in accordance with the present invention.
Figure 11:
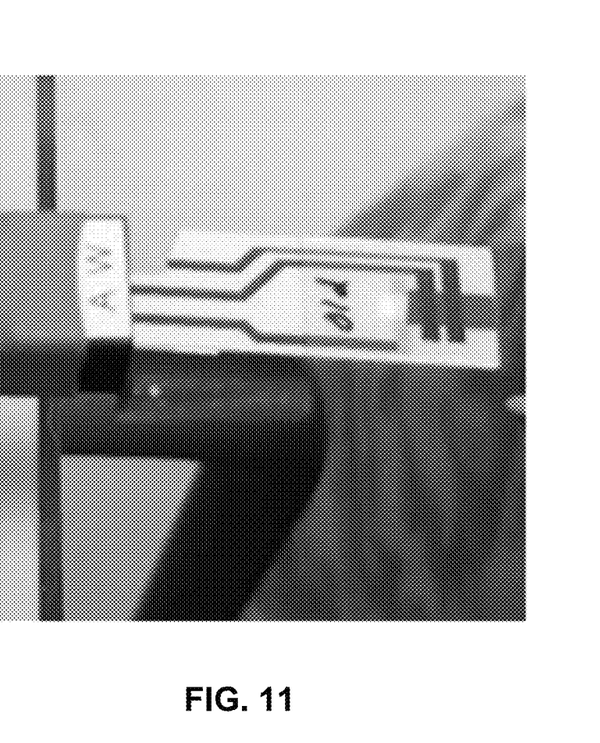
FIG. 11 shows the test strip of FIG. 10 being used in a test.

Referring now to FIG. 10 an exploded perspective view of the electrodes in a test strip made in accordance with the present invention are shown. As seen in FIG. 10, there is a full trigger electrode, a working electrode and a reference electrode. This test strip will be inserted and form part of a screen printed electrode (SPE) in the manner well known in the art, e.g., for glucose strips and the SPE containing the test strip shown in FIG. 10 will be used in the manner described herein. FIG. 11 shows an SPE containing the test strip of FIG. 10 being used in a test.

The present invention provides a point-of-care (POC) in-vitro diagnostic (IVD) device and method for the real-time quantitative assessment of cholinesterase (ChE) enzymatic activity in whole blood for an indication of exposure to ChE inhibiting substances (i.e., chemical warfare nerve agents or carbamate pesticides, or the like). Immediately following exposure typically by being inhaled or via transdermal absorption, cholinesterase inhibitors diffuse into the systemic circulation and rapidly inhibit blood cholinesterase enzymes, acetylcholinesterase (AChE), butyrylcholinesterase (BChE), from within several minutes to hours before overt or observable signs or symptoms can be detected. The duration of this pre-symptomatic window is dependent on the extent of the exposure. The present invention allows assessment of a blood sample during the pre-symptomatic window providing early warning of a suspected exposure and a possible trigger-to-treat with a medical countermeasure.

The present invention can also be utilized to differentiate between types of exposure when symptomatologies can have similar manifestation, such as pinpoint pupils, which can be evident following exposure to other chemical agents besides ChE inhibiting substances.

The diagnostic device and method of the present invention operates and shares many physical attributes of current self-monitoring blood glucose (SMBG) test systems (i.e., glucometer and glucose test strips) known to those skilled in the art. As with SMBG test systems, certain versions of the invention will utilize microliter amounts of capillary blood from a finger stick. Generally, the present invention will only require about 5.04 WB of capillary blood, which is tested without dilution or reagent mixing. The two basic components of the invention are ChE-test strips (similar to glucose test strips), and a hand-held potentiostat (similar to a glucometer) in order to take a measurement. Blood from a lanced finger is being applied to the end of the ChE-test strip allowing the ChE enzymes to mix with reagent(s) dry coated over the surface of printed electrodes. The ChE-test strip will consist either of two (working and pseudo-reference) or three (working, reference, counter) electrodes. The reagents involved in the measurement are preferably but not necessarily dry coated on the electrode surface and therefore no sample preparation or liquid-liquid mixing of any kind is needed prior to assessment. ChE-test strips used in conjunction with the present invention are preferably constructed in a similar physical format as glucose test strips and containing ATCh in the sampling chamber could be used to assess red blood cell AChE activity/inhibition in whole blood samples. A small pocket-sized potentiometer reads the strips after whole blood is obtained via finger stick. Uninhibited blood would have the highest rate of thiocholine production while exposed blood would have a decreased or null thiocholine production depending on the percent inhibition of red blood cell AChE as compared to a personal or average baseline. Since the ChE-test strips would contain no enzyme they would be much less expensive to manufacture than glucose test strips. Acetythiocholine self-contained in the sampling chamber would also be highly stable allowing dramatically longer shelf-lives for ChE-test strips as compared to glucose test strips.

Two possible reagent substrates, acetylthiocholine (ATCh) or butyrylthiocholine (BTCh), can be dry coated on the ChE-test strips depending on the ChE activity (AChE and/or BChE) being assessed. Another reagent component that may be dry coated on the electrodes is bambuterol which is a selective inhibitor of the BChE enzyme and can be used for sole assessments of AChE activity in whole blood. The ChE-test strip may also contain a second set of electrodes to allow simultaneous assessment of blood hematocrit levels for normalization of AChE activity measurements. Data related to blood hematocrit is useful for comparison and assessment of subjects that may be suffering from dehydration or other co-morbidities that can affect AChE activity.

The ChE-test strips form an electrochemical sensor allowing the chemical conversion of ATCh or BTCh to be transduced into an electrical signal, since one of the chemical products of the reaction, known as thiocholine, is electroactive. In certain preferred versions of the present invention, the thiocholine oxidizes cobalt phthalocyanine which in turn undergoes oxidization directly at the carbon electrode surface causing a change in amperage due to the influx of electrons. The amperage change is measured by the hand-held potentiostat via a custom software algorithm and custom hardware.

The present invention therefore provides a point-of-care in-vitro detection test system for indication of chemical warfare nerve agent exposure by assessing cholinesterase activity in a relatively small volume whole blood sample typically but not necessarily obtained via finger stick. The underlying concept of the invention is to harness and leverage the technology and convenience found in self-monitoring blood glucose test systems (i.e., glucometer/glucose test strips) by creating a similarly easy to use and reliable system for use by a first responder or similarly trained personnel, whether on the battlefield, in a civilian setting or otherwise by providing sample-to-answer ease of use (i.e., rapid, minimal burden, low complexity). The key component to the present invention is the composition and chemistry of the electrode system (that is, a working electrode comprising a carbon; reference electrode—Ag/AgCl) in combination with the reagent chemistry coated on the surface of the electrodes allowing specific transduction of cholinesterase enzymatic activity into an electrochemical based signal. The electrode chemistry is a carbon based material impregnated with an electron mediator compound that reduces the voltage potential required to coax electrons from the electroactive reaction product by transferring the electrons to the electrodes resulting in a measurable change in amperage. The test strips disclosed herein have been tested on contrived blood samples (that is, blood spiked with nerve agent) and used to test blood from asymptomatic and symptomatic guinea pigs following exposure. The precise composition of the reagent chemistry coated on the test strips can be tuned for specificity and stability without undue experimentation. Moreover, those skilled in the art will realize that specific chemistries for indication of exposure to other types of chemical warfare agents allowing additional assessments on the same platform are readily made. Complementary technologies such as test strips with the capability of a secondary measurement (i.e., blood hematocrit) and the hand-held potentiostat (i.e., similar to or a modification of a glucometer)

The present invention, among many other advantages, provides a small footprint point-of-care capability that can be integrated into all military Echelon levels of treatment from front-lines to large medical facilities and monitoring laboratories. Current technology deployed by the military for field testing of cholinesterase activity post exposure to cholinesterase inhibiting agents such as organophosphate and carbamate agents is a system that uses a variation of the Ellmans method that can measure either acetylcholinesterase AChE or butyrylcholinesterase BChE activity from isolated blood samples. The present invention represents a vast improvement over the existing technology by providing point-of-care detection and monitoring capability for exposure to AChE inhibiting agents. Aside from the likely scenario of chemical warfare defense (terrorist or battlefield), the present invention can be easily integrated into the military programs regarding occupational safety and health screening programs. Military, Department of Defense civilian and contractor personnel are monitored for ChE activity that includes insecticide controllers around installations and bases and those involved in chemical weapons demilitarization. The present invention correlates to currently available self-monitoring glucose test systems utilizing a small blood sample.

As disclosed herein, the present invention provides an improvement in quality, cost and capability over current cholinesterase activity monitoring systems. Current, deployable systems such as the Test-Mate 400 AChE assay kit described above, consist of multiple components enclosed in a watertight storage case. Aside from the photometric analyzer itself, the kit consists of three boxes along with a detailed package insert. The assay kits contain 48 bottles filled with precisely measured amounts of buffer solution. Box three contains a 96 well erythrocyte reagent plate, 100 capillary tubes (104 volume), 100 filter papers (capillary wipes), a 30 mL clear plastic dropper bottle filled with 18 mL of distilled water and 2 transfer pipettes. In comparison, the present invention incorporates the use of reagents pre-applied and dry-coated to the electrode surface, thus eliminating sample preparation of reagents reducing overall cost and shelf-life of each assay kit. The present invention provides a small-footprint device and system that can be easily carried by military personnel or other users within operational environments to provide an early warning system for exposure to chemical warfare and accidental industrial exposure to cholinesterase inhibiting agents. The present invention is additionally useful for self-monitoring for exposure to agents similar to glucose test systems. The invention also provides a pre-symptomatic exposure detection capability that will allow early intervention of medical countermeasures (MCMs) leading to faster recovery.

The present invention is designed to replace the capability of prior art systems while providing superior operational efficiency at reduced relative cost. The present invention will be low burden, require minimal training to operate, function for self- and buddy-monitoring, and will be fully disposable. The fundamentals established in this work will also support translation of this technology to various other chemical threats (i.e. sulfur mustard, cyanide, opioids) via other types of test articles (i.e. urine, saliva, interstitial fluid) besides whole blood. Other potential uses for the proposed invention therefore include medical response to domestic terrorist or accidental release of industrial cholinesterase inhibiting agents. The present invention is easily integrated into HHS Strategic National Stockpile for chemical agent exposure diagnostics. The primary, non-military application of the invention is related to human exposure to pesticides that inhibit ChE levels that include both organophosphate and carbamate compounds. It is estimated that there are approximately 3 million poisonings and 200,000 deaths per year globally (Jeyaratnam J., 1990, "Acute pesticide poisoning: A major global health problem." World Health Stat Q 43(3): 133-144). The majority of these patients are monitored and or treated within civilian medical facilities and small clinics. The proposed invention could fill a capability gap by providing a quick and easy assay system to detect accidental or intentional exposure to these agents.

The present invention can be used for any situation in which CWNA exposure is a concern. The main focus is use on the battlefield however other sectors of the DoD would potentially utilize the technology. Outside the battlefield the potential users include DHS, first-responders, hospitals, and in the occupational health sector (i.e., pesticide workers).

Although specific examples of the present invention are described above, these should not be construed as limitations to the scope of any invention or of what may be claimed, but rather as descriptions of features that may be specific to particular versions or embodiments of the invention. Certain features that are described above in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations, one or more features from a claimed combination can be implemented separate and apart from the combination, and the resulting combination may be directed to a sub-combination or variation of a sub-combination.

Similarly, while operations for undertaking the diagnostic test described herein, or the steps of constructing the devices disclosed and depicted in the drawings in a particular order, this should not be understood as requiring that such operations be performed in the particular order shown or in sequential order, or that all illustrated operations be perforated, to achieve desirable results. Moreover, the separation of various system components in the embodiments described in this patent document should not be understood as requiring such separation in all embodiments.

It should be understood that only a few embodiments, implementations and examples of the present invention are described above and those skilled in the art will understand that other embodiments, implementations, enhancements and variations can be made based upon that which has been described and illustrated. The scope of the present invention is defined by the claims, which immediately follow.

What is claimed is:

1. A point-of-care in-vitro diagnostic device, comprising:
a potentiostat; and
a test strip being dry coated with at least one reagent, the reagent comprising acetylthiocholine (ATCh) or butyrylthiocholine (BTCh), the test strip being insertable in or communicating with the potentiostat.

2. The device of claim 1, the device quantitatively assessing cholinesterase (ChE) activity in 10.0 µL or less of whole capillary blood (WB).

3. The device of claim 1, wherein the test strip comprises two electrodes.

4. The device of claim 3, wherein the reagent comprises ATCh, the device quantitatively assesses acetylcholinesterase activity, and the test strip further comprises a set of electrodes to allow simultaneous assessment of blood hematocrit levels for normalization of the acetylcholinesterase activity.

5. The device of claim 3, wherein one electrode is comprised of a carbon based material impregnated with an electron mediator compound.

6. The device of claim 1, wherein the test strip comprises three electrodes.

7. The device of claim 1, wherein the test strip comprises an electrochemical sensor which allows chemical conversion of ATCh or BTCh to be transduced into an electrical signal.

8. The device of claim 1, wherein the test strip comprises an electrode system comprising a working electrode and a reference electrode.

9. The device of claim 1, wherein the reagent further comprises a surfactant having a hydrophilic lipophilic balance value between 4 and 20.

10. The device of claim 1, wherein the reagent comprises acetylthiocholine (ATCh) and further comprises bambuterol.

11. The device of claim 1, wherein the reagent comprises butyrylthiocholine (BTCh).

12. The device of claim 1, further comprising an electrode comprising an electron mediator compound.

13. A method for real-time quantitative assessment of cholinesterase (ChE) enzymatic activity in whole blood (WB) for indication of exposure to ChE inhibiting substance, comprising:
contacting the device of claim 1 with whole blood, the whole blood contacting the test strip; and
measuring an electrical signal from chemical conversion of ATCh or BTCh on the test strip with the potentiostat.

14. The method of claim 13, wherein the test strip comprises an electron mediator and an electrode comprising carbon, the electron mediator being deposited on the surface of the electrode, and the chemical conversion of ATCh or BTCh produces thiocholine which oxidizes the electron mediator, thereby producing the electrical signal.

15. The method of claim 13, wherein the ChE inhibiting substance comprises a chemical warfare nerve agent or pesticide.

16. The method of claim 13, wherein the whole blood is 10.0 µL or less of whole capillary blood.

17. The method of claim 13, wherein the whole blood is 5.0 µL or less of whole capillary blood.

18. An electrochemical sensor comprising a test strip dry-coated with at least one reagent, the reagent comprising acetylthiocholine (ATCh) or butyrylthiocholine (BTCh).

19. The electrochemical sensor of claim 18, wherein the reagent further comprises a surfactant having a hydrophilic lipophilic balance value between 4 and 20.

20. A method for real-time quantitative assessment of cholinesterase (ChE) activity in whole blood, comprising:
contacting the whole blood with a test strip comprising:
a reagent comprising acetylchiocholine (ATCh) or butyrylthiocholine (BTCh),
a first electrode comprising carbon and an electron mediator compound, the reagent being dry coated on the first electrode, and
a second electrode; and
measuring an electrical signal from chemical conversion of ATCh or BTCh with a potentiostat, thereby obtaining the real-time quantitative assessment of cholinesterase (ChE) activity in the whole blood.

* * * * *